United States Patent
Kang et al.

(10) Patent No.: US 11,597,705 B2
(45) Date of Patent: Mar. 7, 2023

(54) METHOD FOR PRODUCING 5-METHYL-1H-TETRAZOLE

(71) Applicant: DAEGU CATHOLIC UNIVERSITY INDUSTRY ACADEMIC COOPERATION FOUNDATION, Gyeongsan-si (KR)

(72) Inventors: Dong Wook Kang, Seoul (KR); Jong Yun Jang, Gyeongsangbuk-do (KR); Seong Jeong Lee, Daegu (KR); Jeong In Kim, Chungju-si (KR); Ju Yeon Bae, Yangsan-si (KR); Hyeon Ho Jeon, Incheon (KR); Hee Yoon Ryu, Daegu (KR)

(73) Assignee: DAEGU CATHOLIC UNIVERSITY INDUSTRY COOPERATION FOUNDATION, Gyeongsan-si (KR)

( * ) Notice: Subject to any disclaimer, the term of this patent is extended or adjusted under 35 U.S.C. 154(b) by 0 days.

(21) Appl. No.: 17/568,840

(22) Filed: Jan. 5, 2022

(65) Prior Publication Data
US 2022/0220086 A1    Jul. 14, 2022

(30) Foreign Application Priority Data
Jan. 12, 2021    (KR) .......................... 10-2021-0003934

(51) Int. Cl.
*C07D 257/04*    (2006.01)

(52) U.S. Cl.
CPC .................................. *C07D 257/04* (2013.01)

(58) Field of Classification Search
CPC ..................................................... C07D 257/04
See application file for complete search history.

(56) References Cited

U.S. PATENT DOCUMENTS 5,744,612 A    4/1998    Koguro et al.

FOREIGN PATENT DOCUMENTS

KR    10-2006524 B1    8/2019

OTHER PUBLICATIONS

Demko et al. "Preparation of 5-Substituted 1H-Tetrazoles from Nitriles in Water" J. Org. Chem 66:7945-7950 (2001).

*Primary Examiner* — Kamal A Saeed
(74) *Attorney, Agent, or Firm* — Myers Bigel, P.A.

(57) ABSTRACT

The present invention provides a method for producing high-purity 5-methyl-1H-tetrazole in high yield.

13 Claims, 2 Drawing Sheets

METHOD FOR PRODUCING 5-METHYL-1H-TETRAZOLE

BACKGROUND

1. Technical Field

This application claims the benefit of the filing date of Korean Patent Application No. 10-2021-0003934 filed with the Korean Intellectual Property Office on Jan. 12, 2021, the entire contents of which are incorporated herein by reference.

The present invention relates to a method for producing 5-methyl-1H-tetrazole. Specifically, the present invention relates to a method for producing high-purity 5-methyl-1H-tetrazole in high yield.

2. Related Art

Research on tetrazoles is one of the rapidly expanding fields. These functional groups are used in coordination chemistry as ligands, in medicinal chemistry as metabolically stable surrogates for carboxylic acid groups, and in various materials science applications, including specialty explosives. In addition, substituted tetrazoles having enormous potential are in need of further study.

Among these substituted tetrazoles, alkyl tetrazole is particularly widely used as a corrosion inhibitor in processes for manufacturing semiconductor devices and display devices. However, when this alkyl tetrazole is produced by a conventional method, a problem arises in that the yield thereof is low. In particular, the shorter the length of the alkyl substituent in the tetrazole moiety, the lower the yield is, and hence methyl tetrazole cannot be produced in high yield, and it is difficult to obtain the product in quantitative yield.

Accordingly, there is a need for a method for producing methyl tetrazole in high yield.

SUMMARY

An object of the present invention is to provide a method for producing high-purity 5-methyl-1H-tetrazole in high yield.

However, the object to be achieved by the present invention is not limited to the above-mentioned object, and other objects not mentioned herein will be clearly understood by those skilled in the art from the following description.

According to one aspect of the present invention, there is provided a method for producing 5-methyl-1H-tetrazole, the method including steps of: producing a mixture containing 5-methyl-1H-tetrazole by reacting a reaction mixture containing acetonitrile, an azide compound, a Lewis acid compound, and water; producing a concentrate from the mixture; and obtaining solid 5-methyl-1H-tetrazole by extracting the concentrate 3 to 5 times using ethyl acetate in an amount of 1 ml to 9 ml based on 1 mmol of the azide compound, and drying the extract.

The method for producing 5-methyl-1H-tetrazole according to one embodiment of the present invention may produce 5-methyl-1H-tetrazole in high yield.

The method for producing 5-methyl-1H-tetrazole according to one embodiment of the present invention may produce high-purity 5-methyl-1H-tetrazole.

Effects of the present invention are not limited to the above-described effects, and effects not mentioned herein will be clearly understood by those skilled in the art from the present specification and the accompanying drawings.

DETAILED DESCRIPTION

Figure 1:
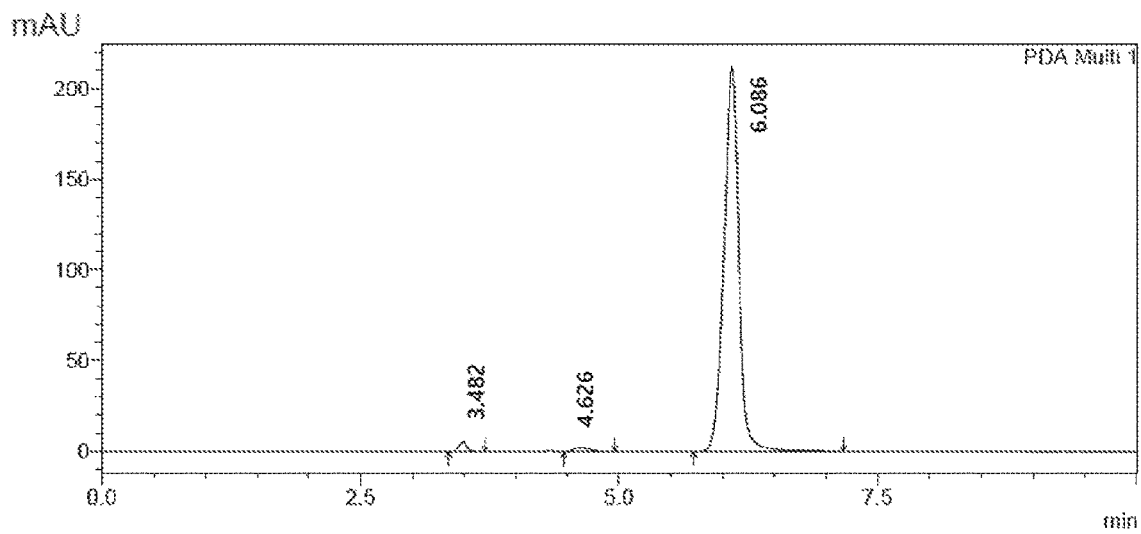
FIGS. 1 and 2 are liquid chromatograms obtained before and after recrystallization, respectively, of 5-methyl-1H-tetrazole produced in Example 1.

Throughout the present specification, it is to be understood that when any part is referred to as "including" any component, it does not exclude other components, but may further include other components, unless otherwise specified.

Throughout the present specification, "A and/or B" means "A and B" or "A or B".

Hereinafter, the present invention will be described in more detail.

According to one embodiment of the present invention, there is provided a method for producing 5-methyl-1H-tetrazole, the method including steps of: producing a mixture containing 5-methyl-1H-tetrazole by reacting a reaction mixture containing acetonitrile, an azide compound, a Lewis acid compound, and water; producing a concentrate from the mixture; and obtaining solid 5-methyl-1H-tetrazole by extracting the concentrate 3 to 5 times using ethyl acetate in an amount of 1 ml to 9 ml based on 1 mmol of the azide compound, and drying the extract.

Hereinafter, each step of the method for producing 5-methyl-1H-tetrazole will be described in detail.

According to one embodiment of the present invention, a mixture containing 5-methyl-1H-tetrazole is first produced by reacting a reaction mixture containing acetonitrile, an azide compound, a Lewis acid compound, and water. The acetonitrile and the azide compound may be contained as reactants for producing 5-methyl-1H-tetrazole, the Lewis acid compound may be contained as a catalyst, and the water may be contained as a solvent in the reaction mixture.

According to one embodiment of the present invention, the azide compound may be a compound capable of forming an azide in the form of a salt. For example, it may include at least one of sodium azide and potassium azide. Preferably, sodium azide may be used as the azide compound.

According to one embodiment of the present invention, the Lewis acid compound may include at least one of zinc chloride, zinc bromide, zinc acetate, trimethylammonium, and copper iodide. Preferably, zinc chloride may be used as the Lewis acid compound.

According to one embodiment of the present invention, the acetonitrile may be contained in the reaction mixture in an amount of 2 mol to 10 mol, 4 mol to 8 mol, or 5 mol to 7 mol, based on 1 mol of the azide compound. When the acetonitrile is used in an amount within the above range, the amount of the acetonitrile as a reactant may be sufficient while the amount of acetonitrile lost due to its low boiling point may be minimized, so that 5-methyl-1H-tetrazole may be produced in high yield.

According to one embodiment of the present invention, the Lewis acid compound may be contained in the reaction mixture in an amount of 0.5 mol to 2 mol, for example, 1 mol, based on 1 mol of the azide compound. The Lewis acid compound serves as a catalyst and is not involved in the reaction itself, but when the Lewis acid compound is used in an amount within the above range, it may be easily removed after completion of the reaction while it is possible to complete enables the reaction quickly and smoothly.

According to one embodiment of the present invention, the water may be contained in the reaction mixture so that the concentration of the azide compound is 0.2 M to 0.5 M. When the water is used in an amount within the above range, it is possible to complete the reaction quickly and to produce 5-methyl-1H-tetrazole with high purity because a separate by-product is not produced.

According to one embodiment of the present invention, the reaction mixture may be added to and reacted in a reaction vessel.

According to one embodiment of the present invention, the reaction mixture may be reacted with stirring, thus producing a mixture containing 5-methyl-1H-tetrazole. The speed of the stirring is not particularly limited, but may preferably be a speed of 100 rpm to 500 rpm.

According to an embodiment of the present invention, the reaction may be a Diels-Alder reaction between the acetonitrile and the azide compound. That is, the Diels-Alder reaction between the acetonitrile and the azide salt may form a tetrazole ring and produce 5-methyl-1H-tetrazole containing a methyl group derived from the methyl group of the acetonitrile.

According to one embodiment of the present invention, the reaction may be performed at a temperature of 80° C. to 110° C., 85° C. to 100° C., or 90° C. to 95° C. When the reaction is performed at a temperature within the above range, the yield of the product may be high because side reactions do not occur, and the reaction may proceed rapidly.

According to one embodiment of the present invention, the reaction temperature may be controlled by increasing the temperature of a bath in which the reaction vessel is immersed. When the reaction temperature is controlled by immersing the reaction vessel in the bath, it is possible to maintain the temperature so that the reaction may be performed at a constant temperature, and thus the yield of the product may be high.

According to one embodiment of the present invention, the reaction may be performed for 10 hours to 30 hours, 10 hours to 20 hours, or 15 hours to 18 hours. When the reaction is performed for a time within the above range, it is possible to produce 5-methyl-1H-tetrazole in high yield.

After completion of the reaction, the mixture containing 5-methyl-1H-tetrazole may be cooled to room temperature. The method of cooling the mixture is not limited, and the mixture may be cooled by allowing it to stand or cooled using a cooler or cooling water.

According to one embodiment of the present invention, a concentrate is then produced from the mixture.

According to one embodiment of the present invention, the step of producing the concentrate may include steps of: forming an insoluble salt by removing water from the mixture and adding a basic aqueous solution to the mixture from which the water has been removed; preparing an acidic dispersion containing 5-methyl-1H-tetrazole, a water-soluble salt and water by removing the insoluble salt by filtration and adding a strongly acidic aqueous solution to the filtrate; and concentrating the acidic dispersion under reduced pressure to remove the water.

According to one embodiment of the present invention, water may be removed under reduced pressure after cooling of the mixture. In this case, the amount of water removed may be equal to or smaller than the amount of water added in the production of the reaction mixture.

According to one embodiment of the present invention, the catalyst may be removed by adding a basic aqueous solution after removal of the water. After completion of the reaction, a basic aqueous solution may be added to remove the catalyst that is no longer needed. The basic aqueous solution may be an aqueous metal hydroxide solution, and may contain, for example, sodium hydroxide, potassium hydroxide, calcium hydroxide, or the like.

According to one embodiment of the present invention, a basic aqueous solution may be added to form sediment, that is, an insoluble salt. Since the basic aqueous solution contains hydroxide ions, it can react with the cation of the Lewis acid to form sediment, which is an insoluble salt, and may easily remove the Lewis acid used as a catalyst.

According to one embodiment of the present invention, when the basic aqueous solution is added, for example, the reaction shown in Reaction Formula 1 below may proceed. That is, when zinc chloride is used as the Lewis acid and an aqueous sodium hydroxide solution is used as the basic aqueous solution, the reaction shown in Reaction Formula 1 below may proceed to form zinc hydroxide as an insoluble salt, which makes it possible to remove zinc used as the catalyst.

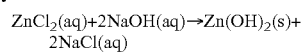
[Reaction Formula 1]

According to one embodiment of the present invention, the basic aqueous solution may be added in an amount of 3 to 10 equivalents per equivalent of the Lewis acid. For example, when the Lewis acid is zinc chloride, the basic aqueous solution may be added in an amount of 1 to 3 equivalents per equivalent of zinc chloride. When the basic aqueous solution is added in an amount within the above range, zinc hydroxide may be easily formed and removed, and thus the purity of 5-methyl-1H-tetrazole as a final product may be high.

According to one embodiment of the present invention, stirring may be performed for 1 to 3 hours after addition of the basic aqueous solution. During this stirring, zinc hydroxide may be easily formed and removed, and thus the purity of 5-methyl-1H-tetrazole as a final product may be high.

According to one embodiment of the present invention, an acidic dispersion may be prepared by removing the insoluble salt by filtration and adding a strongly acidic aqueous solution to the filtrate. The acidic dispersion may contain 5-methyl-1H-tetrazole, a water-soluble salt, and water. The insoluble salt is not soluble in water, and thus may be removed by filtration. The filtrate may contain 5-methyl-1H-tetrazole formed by the reaction. When the strongly acidic aqueous solution is added to the filtrate, the acidic dispersion may contain may contain a water-soluble salt formed from the cation of the basic aqueous solution and the anion of the strongly acidic aqueous solution.

The strongly acidic aqueous solution is added to acidify the filtrate, and may contain a strong acid, such as sulfuric acid, hydrochloric acid or hydrofluoric acid, as a strongly acidic material capable of providing hydrogen ions, and is particularly limited as long as it is used in the art.

According to one embodiment of the present invention, the strongly acidic aqueous solution may be added so that the pH of the filtrate reaches 2 to 3. When a strongly acidic aqueous solution is added so that the filtrate has a pH within the above range, 5-methyl-1H-tetrazole having a low pKa value may be extracted with high efficiency.

Next, the acidic dispersion may be concentrated under reduced pressure to remove water therefrom. When water is removed from the acidic dispersion, the concentrate may contain 5-methyl-1H-tetrazole and a water-soluble salt formed from a cation derived from the azide compound and an anion derived from the Lewis acid compound.

According to one embodiment of the present invention, the water may be removed so that the volume of the acidic solution is 10% to 20%.

Next, the concentrate is extracted with ethyl acetate and dried to obtain solid 5-methyl-1H-tetrazole. The concentrate may contain 5-methyl-1H-tetrazole and a water-soluble salt formed from a cation derived from the azide compound and an anion derived from the Lewis acid compound. Using a difference in solubility in that 5-methyl-1H-tetrazole has high solubility in ethyl acetate, whereas the water-soluble salt has low solubility in ethyl acetate, 5-methyl-1H-tetrazole may be extracted with high efficiency.

According to one embodiment of the present invention, the solubility of 5-methyl-1H-tetrazole in ethyl acetate may be 100,000 to 250,000 times the solubility of the water-soluble salt in ethyl acetate. When there is a difference in solubility within the above range, 5-methyl-1H-tetrazole may be extracted with high efficiency.

According to one embodiment of the present invention, solid 5-methyl-1H-tetrazole may be obtained by extracting the concentrate 3 to 5 times using ethyl acetate in an amount of 1 ml to 9 ml based on 1 mmol of the azide compound, and drying the extract. When the extraction is performed in an ethyl acetate amount and extraction number within the above ranges, 5-methyl-1H-tetrazole may be extracted with high efficiency so that the amount thereof lost may be minimized, and the yield of 5-methyl-1H-tetrazole as a final product may be high.

According to one embodiment of the present invention, solid 5-methyl-1H-tetrazole may be obtained by drying the organic layer, extracted with ethyl acetate, using magnesium sulfate.

According to one embodiment of the present invention, the yield of solid 5-methyl-1H-tetrazole may be 65% to 95% based on the reactants. That is, the yield of 5-methyl-1H-tetrazole in the method for producing 5-methyl-1H-tetrazole according to one embodiment of the present invention may be as high as 65% to 95%, 70% to 95%, or 85% to 95%.

According to one embodiment of the present invention, the purity of solid 5-methyl-1H-tetrazole may be 95% to 98%. That is, the purity of 5-methyl-1H-tetrazole produced by the method for producing 5-methyl-1H-tetrazole according to one embodiment of the present invention may be as high as 95% to 98%.

The method for producing 5-methyl-1H-tetrazole according to one embodiment of the present invention may further include, after the step of obtaining solid 5-methyl-1H-tetrazole, a step of recrystallization from a methyl chloride or ether-based solvent. Through the recrystallization, the purity of 5-methyl-1H-tetrazole may be further increased.

According to one embodiment of the present invention, the step of recrystallization may include a step of adding a methyl chloride or ether-based solvent in an amount of 5 ml to 15 ml per g of the solid 5-methyl-1H-tetrazole, followed by stirring under reflux.

The reflux is a method of making a volatile material or solvent flowable in a liquid state by liquefaction from above by means of a cooler or the like provided to prevent the volatile material or solvent from volatilizing during continuous heating. Through this reflux, the solid 5-methyl-1H-tetrazole may be dissolved in a methyl chloride or ether-based solvent at a high temperature, and then volatile impurities and the like thereof may be removed.

After completion of the heating under reflux, the solid precipitated by cooling to room temperature may be filtered to obtain 5-methyl-1H-tetrazole again.

According to one embodiment of the present invention, the purity of 5-methyl-1H-tetrazole obtained through the recrystallization may be 95% to 99.99%, or 98% to 99.99%. As other impurities are additionally removed through the recrystallization, the purity of 5-methyl-1H-tetrazole may be increased compared to that before the recrystallization.

Hereinafter, the present invention will be described in detail with reference to examples. However, the examples according to the present invention may be modified into various different forms, and the scope of the present invention is not interpreted as being limited to the examples described below. The examples of the present specification are provided to more completely explain the present invention to those skilled in the art.

Example 1

Acetonitrile (19.05 g, 464 mmol, 8.0 eq.), water (125 mL), sodium azide (3.78 g, 58 mmol, 1.0 eq.), zinc chloride (8.2 g, 58 mmol, 1.0 eq.) were placed and mixed together in a 1-L volume round bottom flask at room temperature, thus preparing a reaction mixture. The flask was placed in a bath and stirred for 16 hours at a bath temperature of 110° C. At this time, the temperature inside the flask was 85° C.

Next, the solution inside the flask was cooled to room temperature, and then 125 mL of water was removed under reduced pressure, and 250 mL of a 5 wt % NaOH aqueous solution was added and the mixture was stirred for 2 hours. After stirring, the formed solid zinc hydroxide was removed by filtration through a celite pad.

An acidic solution was prepared by adding 25 mL of 37 wt % hydrochloric acid slowly to the filtrate from which zinc hydroxide has been removed so that the pH of the solution reached 2.5. The acidic solution was concentrated under reduced pressure to remove 243 mL of water therefrom, and the remaining concentrate was extracted 4 times with 500 mL of ethyl acetate.

After completion of the extraction, the organic layer was dried with $MgSO_4$ and filtered. The filtrate was concentrated and the resulting white solid was dried under reduced pressure to obtain 5-methyl-1H-tetrazole (4.55 g, 88% yield).

Additional Examples and Comparative Examples

In each of Examples 2 to 5 and Comparative Examples 1 to 6, 5-methyl-1H-tetrazole was produced in the same manner as in Example 1, except that reaction mixtures were prepared using controlled amounts of acetonitrile and sodium azide, and controlled types and amounts of Lewis acid and solvent, which were controlled as shown in Table 1 below, and that the reaction temperature was controlled.

The yields of 5-methyl-1H-tetrazole in Examples 2 to 5 and Comparative Examples 1 to 6 are also shown in Table 1.

TABLE 1

| | ACN | NaN$_3$ | Lewis acid | | Solvent | | Reaction temperature | Yield |
|---|---|---|---|---|---|---|---|---|
| Example 1 | 19.05 g | 3.78 g | ZnCl$_2$ | 8.20 g | Water | 125 mL | 110° C. | 88% |
| Example 2 | 23.85 g | 3.78 g | ZnCl$_2$ | 8.20 g | Water | 125 mL | 110° C. | 48% |
| Example 3 | 14.36 g | 3.78 g | ZnCl$_2$ | 8.20 g | Water | 125 mL | 110° C. | 69% |
| Example 4 | 9.44 g | 7.49 g | ZnCl$_2$ | 15.78 g | Water | 250 mL | 110° C. | 55% |
| Example 5 | 14.16 g | 7.49 g | ZnCl$_2$ | 15.78 g | Water | 250 mL | 110° C. | 74% |
| Comparative Example 1 | 9.52 g | 3.78 g | ZnCl$_2$ | 8.20 g | Ethanol | 125 mL | 110° C. | 6% |
| Comparative Example 2 | 9.59 g | 3.78 g | ZnCl$_2$ | 8.20 g | Ethanol | 125 mL | 110° C. | 38% |
| Comparative Example 3 | 9.44 g | 7.48 g | ZnCl$_2$ | 15.68 g | n-butanol | 250 mL | 110° C. | 90% |
| Comparative Example 4 | 9.59 g | 3.77 g | ZnCl$_2$ | 7.91 g | n-butanol | 125 mL | 110° C. | 62% |
| Comparative Example 5 | 19.04 g | 7.54 g | ZnAc | 25.46 g | n-butanol | 250 mL | 110° C. | 62% |
| Comparative Example 6 | 19.04 g | 7.54 g | ZnAc | 25.46 g | n-butanol | 250 mL | 110° C. | 48 |

In Table 1, ACN denotes acetonitrile, NaN$_3$ denotes sodium azide, ZnCl$_2$ denotes zinc chloride, and ZnAc denotes zinc acetate.

Referring to Table 1 above, it can be confirmed that the yields of methyl tetrazole in Examples 1 to 5 were high, and in particular, the yields of methyl tetrazole in Examples 1, 3 and 5 were high.

Evaluation of Purity by Liquid Chromatography

Liquid chromatography of 5-methyl-1H-tetrazole produced in Example 1 was performed, and the purity thereof was measured from the chromatogram. The purity of 5-methyl-1H-tetrazole produced in Example 1 was 97.7%.

40 mL of methyl chloride was added to 4.0 g of 5-methyl-1H-tetrazole produced in Example 1, and the mixture was stirred under reflux and then cooled to room temperature. Next, the solid was filtered and dried under reduced pressure to obtain 5-methyl-1H-tetrazole (3.77 g, 94% yield). After recrystallization of 5-methyl-1H-tetrazole produced in Example 1, liquid chromatography thereof was performed in the same manner as above, and the purity thereof was measured from the chromatogram. The purity of 5-methyl-1H-tetrazole after recrystallization was 99.97%.

Figure 2:
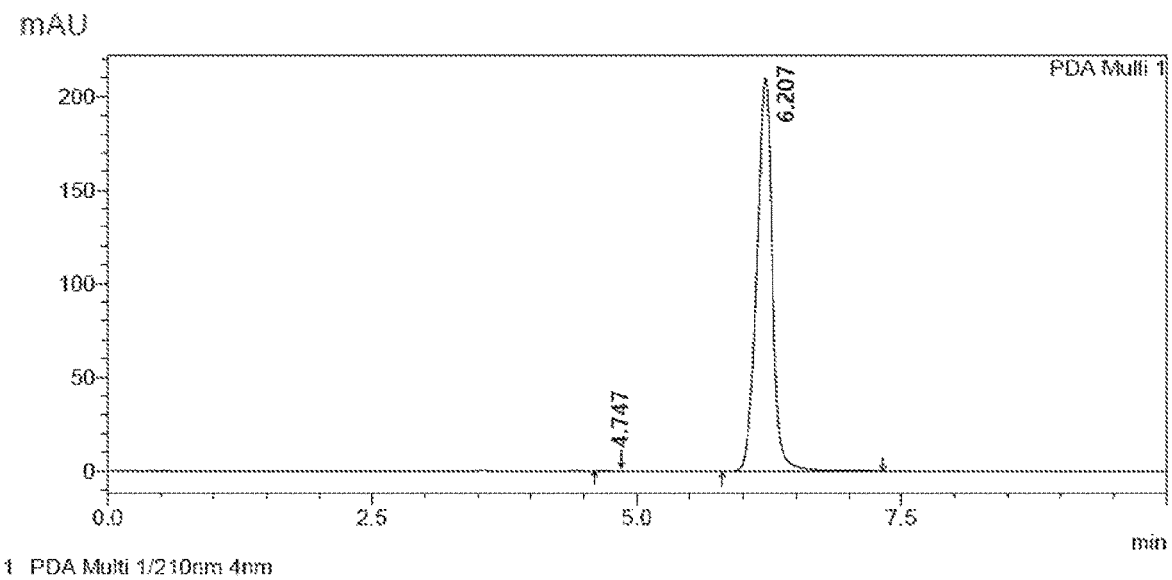

FIGS. 1 and 2 show liquid chromatograms obtained before and after recrystallization, respectively, of 5-methyl-1H-tetrazole produced in Example 1.

Referring to Table 1 above and FIGS. 1 and 2, it can be confirmed that 5-methyl-1H-tetrazole produced in Example 1 was obtained in high yield, and the purity thereof was very high, and the purity thereof could be increased to about 100% through recrystallization.

Although the present disclosure has been described above by way of limited embodiments, the present disclosure is not limited thereto. It should be understood that the present disclosure can be variously changed and modified by those skilled in the art without departing from the technical sprit of the present disclosure and the range of equivalents to the appended claims.

What is claimed is:

1. A method for producing 5-methyl-1H-tetrazole, the method comprising steps of:
   producing a mixture containing 5-methyl-1H-tetrazole by reacting a reaction mixture containing acetonitrile, an azide compound, a Lewis acid compound, and water;
   producing a concentrate from the mixture; and
   obtaining solid 5-methyl-1H-tetrazole by extracting the concentrate 3 to 5 times using ethyl acetate in an amount of 1 ml to 9 ml based on 1 mmol of the azide compound, and drying the extract.

2. The method of claim 1, wherein the azide compound comprises at least one of sodium azide and potassium azide.

3. The method of claim 1, wherein the Lewis acid compound comprises at least one of zinc chloride, zinc bromide, zinc acetate, trimethylammonium, and copper iodide.

4. The method of claim 1, wherein the acetonitrile is contained in the reaction mixture in an amount of 2 mol to 10 mol based on 1 mol of the azide compound.

5. The method of claim 1, wherein the Lewis acid compound is contained in the reaction mixture in an amount of 0.5 mol to 2 mol based on 1 mol of the azide compound.

6. The method of claim 1, wherein the water is contained in the reaction mixture so that a concentration of the azide compound is 0.2 M to 0.5 M.

7. The method of claim 1, wherein the reaction is performed at a temperature of 80° C. to 110° C.

8. The method of claim 1, wherein the reaction is performed for 10 hours to 30 hours.

9. The method of claim 1, wherein the step of producing the concentrate comprises steps of:
   forming an insoluble salt by removing water from the mixture and adding a basic aqueous solution to the mixture from which the water has been removed;
   preparing an acidic dispersion containing 5-methyl-1H-tetrazole, a water-soluble salt and water by removing the insoluble salt by filtration and adding a strongly acidic aqueous solution to the filtrate; and
   concentrating the acidic dispersion under reduced pressure to remove the water therefrom.

10. The method of claim 1, further comprising, after the step of obtaining the solid 5-methyl-1H-tetrazole, a step of recrystallization from a methyl chloride or ether-based solvent.

11. The method of claim 10, wherein the step of recrystallization comprises a step of adding the methyl chloride or ether-based solvent in an amount of 5 ml to 15 ml per g of the solid 5-methyl-1H-tetrazole, followed by stirring under reflux.

12. The method of claim 1, wherein a yield of 5-methyl-1H-tetrazole in the method is 65% to 95%.

13. The method of claim 1, wherein a purity of 5-methyl-1H-tetrazole produced by the method is 95% to 99.99%.

* * * * *